(12) United States Patent
Meulink et al.

(10) Patent No.: US 9,980,828 B2
(45) Date of Patent: May 29, 2018

(54) MODULAR ORTHOPAEDIC COMPONENTS

(75) Inventors: Steven L. Meulink, Warsaw, IN (US);
Ryan D. Schlotterback, Warsaw, IN (US); Barish Banerjee, Kolkata (IN); Stephen J. Vankoski, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 360 days.

(21) Appl. No.: 12/486,791

(22) Filed: Jun. 18, 2009

(65) Prior Publication Data
US 2009/0270996 A1 Oct. 29, 2009

Related U.S. Application Data

(63) Continuation of application No. 11/616,369, filed on Dec. 27, 2006, now abandoned, which is a
(Continued)

(51) Int. Cl.
*A61B 5/00* (2006.01)
*A61F 2/46* (2006.01)
(Continued)

(52) U.S. Cl.
CPC .............. *A61F 2/46* (2013.01); *A61B 50/30* (2016.02); *A61F 2/0095* (2013.01); *A61F 2/3609* (2013.01); *A61B 5/107* (2013.01); *A61B 5/4528* (2013.01); *A61B 50/33* (2016.02); *A61B 2050/3008* (2016.02); *A61F 2/38* (2013.01); *A61F 2/40* (2013.01); *A61F 2002/30332* (2013.01); *A61F 2002/30604* (2013.01); *A61F 2002/30616* (2013.01); *A61F 2002/30708* (2013.01); *A61F 2002/30714* (2013.01);
(Continued)

(58) Field of Classification Search
CPC . A61B 2034/105; A61B 17/164; A61B 34/25;
A61B 17/1617; A61B 17/1684; A61B 17/1703; A61B 17/15; A61B 17/1664; A61B 17/1668; A61B 17/175; A61B 17/1778; A61B 2017/00477; A61B 2017/0275; A61B 17/155
USPC .......................................... 623/21.11–22.39
See application file for complete search history.

(56) References Cited

U.S. PATENT DOCUMENTS 4,957,510 A * 9/1990 Cremascoli ................ 623/22.46
5,480,439 A   1/1996 Bisek et al.
(Continued)

OTHER PUBLICATIONS

Zimmer VerSys® Hip System—VerSys® Collared Beaded MidCoat Template Data Sheet Size 10—Size 20.
(Continued)

*Primary Examiner* — Ann Schillinger
(74) *Attorney, Agent, or Firm* — Schwegman Lundberg & Woessner, P.A.

(57) ABSTRACT

Modular neck components for hip implants having independent variables associated with physical characteristics of the implant, including leg length, offset, and anteversion. During surgery, the surgeon may be confronted with a need to change a preoperatively-chosen modular neck. For example, the surgeon may desire a change in at least one of the variables, e.g., leg length, offset, and/or anteversion. The present disclosure allows the surgeon to quickly and easily select a different modular neck based on an evaluation of one of the variables without requiring reevaluation of the other variables.

19 Claims, 8 Drawing Sheets

Related U.S. Application Data continuation-in-part of application No. 11/458,257, filed on Jul. 18, 2006, now abandoned.

(51) Int. Cl.

| | | |
|---|---|---|
| *A61F 2/00* | (2006.01) | |
| *A61F 2/36* | (2006.01) | |
| *A61B 50/30* | (2016.01) | |
| *A61B 5/107* | (2006.01) | |
| *A61F 2/38* | (2006.01) | |
| *A61F 2/40* | (2006.01) | |
| *A61F 2/30* | (2006.01) | |
| *A61B 50/33* | (2016.01) | |

(52) U.S. Cl.
CPC ............... *A61F 2002/30948* (2013.01); *A61F 2002/30963* (2013.01); *A61F 2002/365* (2013.01); *A61F 2002/3611* (2013.01); *A61F 2002/3625* (2013.01); *A61F 2002/3652* (2013.01); *A61F 2002/4633* (2013.01); *A61F 2220/0033* (2013.01); *A61F 2250/0084* (2013.01); *A61F 2250/0089* (2013.01)

(56) References Cited

U.S. PATENT DOCUMENTS

| 5,597,384 | A | | 1/1997 | Walker et al. | |
|---|---|---|---|---|---|
| 5,800,556 | A | * | 9/1998 | Sanders et al. | 623/22.45 |
| 6,464,728 | B1 | * | 10/2002 | Murray | A61F 2/30734 |
| | | | | | 623/22.42 |
| 6,991,655 | B2 | | 1/2006 | Iversen | |
| 8,202,324 | B2 | | 6/2012 | Meulink et al. | |
| 8,428,693 | B2 | | 4/2013 | Meulink | |
| 8,845,749 | B2 | | 9/2014 | Meulink et al. | |
| 2004/0138754 | A1 | | 7/2004 | Lang et al. | |
| 2004/0147926 | A1 | | 7/2004 | Iversen | |
| 2004/0171924 | A1 | | 9/2004 | Mire et al. | |
| 2004/0243481 | A1 | | 12/2004 | Bradbury et al. | |
| 2005/0054917 | A1 | | 3/2005 | Kitson | |
| 2005/0065533 | A1 | | 3/2005 | Magen et al. | |
| 2005/0085714 | A1 | | 4/2005 | Foley et al. | |
| 2005/0203384 | A1 | | 9/2005 | Sati et al. | |
| 2006/0065533 | A1 | | 3/2006 | Inoue et al. | |
| 2006/0173548 | A1 | * | 8/2006 | Auxepaules et al. | 623/22.12 |
| 2007/0066917 | A1 | | 3/2007 | Hodorek et al. | |
| 2007/0118243 | A1 | | 5/2007 | Schroeder et al. | |
| 2007/0179626 | A1 | | 8/2007 | de la Barrera et al. | |
| 2007/0233269 | A1 | | 10/2007 | Steines et al. | |
| 2008/0021567 | A1 | | 1/2008 | Meulink et al. | |
| 2008/0058945 | A1 | | 3/2008 | Hajaj et al. | |
| 2008/0077003 | A1 | | 3/2008 | Barth et al. | |
| 2012/0221114 | A1 | | 8/2012 | Meulink et al. | |
| 2013/0079888 | A1 | | 3/2013 | Meulink | |

OTHER PUBLICATIONS

Wright Profemur® Z Total Hip System Surgical Technique Brochure.
Wright Profemur® Z/Plasma Z Total Hip System Surgical Technique Brochure.
DePuy Corail® Total Hip System Surgical Technique Brochure.
Product Brochure—Zimmer VerSys$^{SM}$ Hip System Fiber Metal Taper Hip Prosthesis.
Zimmer VerSys$^{SM}$ Versys Fiber Metal Midcoat and Beaded Midcoat Hip Prosthesis Surgical Technique Brochure.
Profemur Z Abbreviated Surgical Technique, Wright Medical Technology, 2 pages, 2003 (Profemur).
Brochure—Zimmer M/L Taper Hip Prosthesis with Kinectiv Technology, Zimmer 2007, 2008, 97-7713-001-00.
Surgical Technique—Zimmer M/L Taper Hip Prosthesis with Kinectiv Technology, Zimmer 2007, 2008, 97-7713-002-00.
Brochure—Zimmer ZMR Hip System, Zimmer 2004, 2008, 97-9990-201-00.
Performance Evaluation of Kinectiv Technology, Hertzler et al., Zimmer 2008, 97-7713-010-00.
Surgical Technique—Wright Profemur Z, Total Hip System, Wright Medical Technology, Inc.
"U.S. Appl. No. 11/458,257, Examiner Interview Summary dated Jan. 1, 2009", 11 pgs.
"U.S. Appl. No. 11/458,257, Final Office Action dated Dec. 24, 2008", 7 pgs.
"U.S. Appl. No. 11/458,257, Non-Final Office Action dated Apr. 2, 2009", 8 pgs.
"U.S. Appl. No. 11/458,257, Non-Final Office Action dated May 13, 2008", 6 pgs.
"U.S. Appl. No. 11/458,257, Non-Final Office Action dated Oct. 14, 2009", 6 pgs.
"U.S. Appl. No. 11/458,257, Response filed Mar. 24, 2009 to Final Office Action dated Dec. 24, 2008", 13 pgs.
"U.S. Appl. No. 11/458,257, Response filed Jul. 2, 2009 to Non-Final Office Action dated Apr. 2, 2009", 12 pgs.
"U.S. Appl. No. 11/458,257, Response filed Sep. 15, 2008 to Non-Final Office Action dated May 13, 2008", 8 pgs.
"U.S. Appl. No. 11/616,369, Non Final Office Action dated Sep. 15, 2009", 8 pgs.
"U.S. Appl. No. 12/723,134, Non-Final Office Action dated Oct. 14, 2010", 7 pgs.
"U.S. Appl. No. 12/758,423, Final Office Action dated Aug. 17, 2011", 11 pgs.
"U.S. Appl. No. 12/758,423, Final Office Action dated Sep. 20, 2012", 9 pgs.
"U.S. Appl. No. 12/758,423, Non Final Office Action dated Mar. 3, 2011", 11 pgs.
"U.S. Appl. No. 12/758,423, Non Final Office Action dated Mar. 30, 2012", 8 pgs.
"U.S. Appl. No. 12/758,423, Notice of Allowance dated Dec. 24, 2012", 8 pgs.
"U.S. Appl. No. 12/758,423, Preliminary Amendment dated Mar. 16, 2010", 7 pgs.
"U.S. Appl. No. 12/758,423, Response filed Jan. 10, 2012 to Restriction Requirement dated Nov. 10, 2011", 3 pgs.
"U.S. Appl. No. 12/758,423, Response filed Jun. 3, 2011 to Non Final Office Action dated Mar. 3, 2011", 12 pgs.
"U.S. Appl. No. 12/758,423, Response filed Jul. 2, 2012 to Non Final Office Action dated Mar. 30, 2012", 10 pgs.
"U.S. Appl. No. 12/758,423, Response filed Nov. 1, 2011 to Final Office Action", 15 pgs.
"U.S. Appl. No. 12/758,423, Response filed Nov. 14, 2012 to Final Office Action dated Sep. 20, 2012", 10 pgs.
"U.S. Appl. No. 12/758,423, Restriction Requirement dated Nov. 10, 2011", 9 pgs.
"U.S. Appl. No. 13/046,849, Application Interview Summary dated Oct. 21, 2011", 3 pgs.
"U.S. Appl. No. 13/046,849, Final Office Action dated Feb. 2, 2012", 9 pgs.
"U.S. Appl. No. 13/046,849, Non Final Office Action dated Jul. 25, 2011", 8 pgs.
"U.S. Appl. No. 13/046,849, Notice of Allowance dated Apr. 3, 2012", 7 pgs.
"U.S. Appl. No. 13/046,849, Response filed Mar. 20, 2012 to Final Office Action", 10 pgs.
"U.S. Appl. No. 13/046,849, Response filed Nov. 1, 2011 to Non Final Office Action dated Jul. 25, 2011", 12 pgs.
"U.S. Appl. No. 13/465,454, Response filed Mar. 25, 2013 to Final Office Action dated Jan. 25, 2013", 10 pgs.
"U.S. Appl. No. 13/465,454, Response filed Dec. 17, 2012 to Non Final Office Action dated Sep. 18, 2012", 9 pgs.
"U.S. Appl. No. 13/465,454, Advisory Action dated Apr. 8, 2013", 2 pgs.
"U.S. Appl. No. 13/465,454, Final Office Action dated Jan. 25, 2013", 9 pgs.
"U.S. Appl. No. 13/465,454, Non Final Office Action dated Sep. 18, 2012", 10 pgs.

(56) References Cited

OTHER PUBLICATIONS

"U.S. Appl. No. 13/465,454, Response filed May 23, 2013 to Advisory Action dated Apr. 8, 2013", 10 pgs.

"Zimmer VerSys Hip System, Fiber Metal Taper HP Prosthesis", Versatile Total Hip Solutions Using Proven Designs and Enhanced Fixation, 97-7862-01 20 MIP, Zimmer, Inc., (1997), 4 pgs.

"U.S. Appl. No. 13/465,454, Notice of Allowability dated Aug. 11, 2014", 7 pgs.

"U.S. Appl. No. 13/465,454, Notice of Allowance dated May 7, 2014", 10 pgs.

"U.S. Appl. No. 13/465,454, Response filed Jan. 27, 2014 to Non-Final Office Action dated Sep. 26, 2013", 10 pgs.

"U.S. Appl. No. 13/683,017, Examiner Interview Summary dated May 10, 2016", 4 pgs.

"U.S. Appl. No. 13/683,017, Final Office Action dated Jun. 2, 2016", 11 pgs.

"U.S. Appl. No. 13/683,017, Non Final Office Action dated Sep. 29, 2015", 10 pgs.

"U.S. Appl. No. 13/683,017, Response filed Mar. 21, 2016 to Non Final Office Action dated Sep. 29, 2015", 16 pgs.

"U.S. Appl. No. 13/683,017, Response filed Nov. 2, 2016 to Final Office Action dated Jun. 2, 2016", 16 pgs.

\* cited by examiner

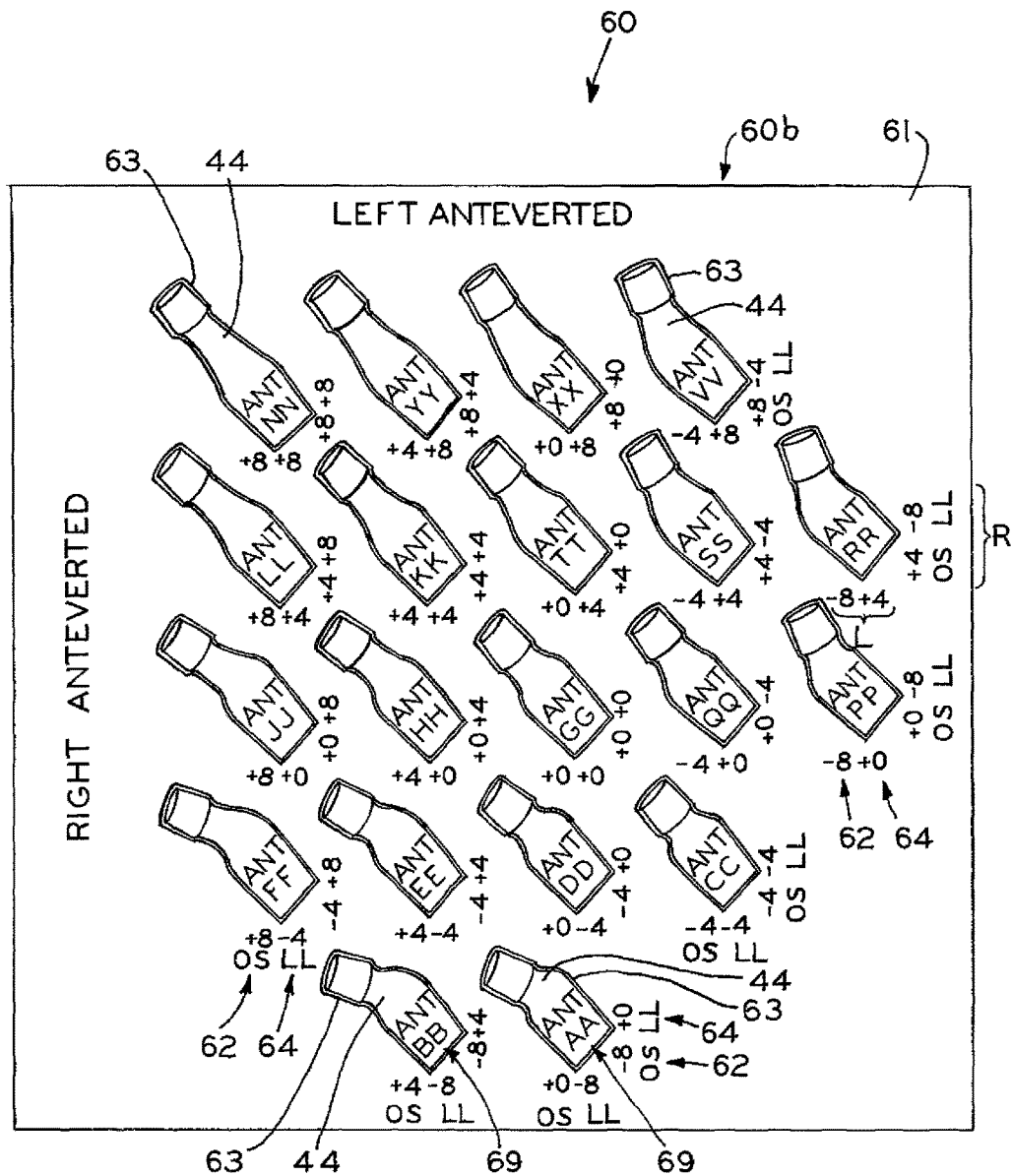
FIG_5B

MODULAR ORTHOPAEDIC COMPONENTS

CROSS-REFERENCE TO RELATED APPLICATIONS

This application is a continuation of U.S. patent application Ser. No. 11/458,257, filed Jul. 18, 2006, entitled METHOD FOR SELECTING MODULAR IMPLANT COMPONENTS, and U.S. patent application Ser. No. 11/616,369, filed Dec. 27, 2006, entitled MODULAR ORTHOPAEDIC COMPONENT CASE, both assigned to the assignee of the present application, the disclosures of which are hereby expressly incorporated herein by reference.

BACKGROUND

1. Field of the Invention

The present invention relates to modular components for prosthetic joints. More particularly, the present invention relates to modular neck components for prosthetic hip joints.

2. Description of the Related Art

Orthopaedic prosthetic implants are commonly used to replace some or all of a patient's hip joint in order to restore the use of the hip joint, or to increase the use of the hip joint, following deterioration due to aging or illness, or injury due to trauma. In a hip replacement, or hip arthroplasty procedure, a femoral component is used to replace a portion of the patient's femur, including the femoral neck and head. The femoral component is typically a hip stem, which includes a stem portion positioned within the prepared femoral canal of the patient's femur and secured via bone cement, or by a press-fit followed by bony ingrowth of the surrounding tissue into a porous coating of the stem portion. The hip stem also includes a neck portion adapted to receive a prosthetic femoral head. The femoral head may be received within a prosthetic acetabular component, such as an acetabular cup received within the prepared recess of the patient's acetabulum.

Orthopaedic implants for hip replacement may include modular hip joint components. For example, the hip stem and the neck portion with femoral head are formed as separate components. Prior to an operation, a surgeon chooses a hip stem and a neck portion based on patient anatomy, body image scans, and/or other patient-specific data. However, during surgery, the surgeon may discover that a different hip stem or a different neck portion is desired to provide more optimum results. Modular hip joint components allow the surgeon to choose a different hip stem or neck portion depending on the specific application and needs of the patient and surgeon. Typically, the surgeon will only change the neck portion because the hip stem is usually implanted first, and removal of the hip stem from the femoral intramedullary canal is generally undesirable. Thus, the neck portion is usually the component that is most often changed intraoperatively. The surgeon may be provided with a number of different neck portions to accommodate various patient anatomies.

In one known system, for example, the surgeon chooses from a plurality of options to replace an existing neck portion with an alternative neck portion to provide the best outcome for the patient. The surgeon's choices rely on the location of the center of rotation of the femoral head component of the implant. Referring to FIG. 1, an image of a proximal femur 20 is shown and includes femoral head 22, greater trochanter 24, lesser trochanter 26, femoral neck 28, and a portion of femoral shaft 27. FIG. 1 illustrates a portion 30 of a template used in the known system. The template may also include images of the femur, similar to those described below with reference to FIGS. 3 and 4. Portion 30 of the template may be placed over the image of proximal femur 20 acquired preoperatively to plan the optimum location of the center of the femoral head of the implant. Portion 30 of the template may include a plurality of reference points 32, 34 arranged in a generally fan-shaped arrangement. Each reference point represents the center of rotation for the femoral head component of the implant. Typically, reference points 32, 34 may be based on a spherical or cylindrical coordinate system. If the surgeon desires an intra-operative change which differs from the preoperatively chosen modular neck portion, the surgeon must simultaneously evaluate at least three variables based on the center of rotation of the femoral head of the implant, and may need to consult various tables to evaluate these variables based on physical characteristics of the patient in order to choose an optimal implant.

SUMMARY

The present invention provides modular neck components for hip implants having independent variables associated with physical characteristics of the implant, including leg length, offset, and anteversion. During surgery, the surgeon may be confronted with a need to change a preoperatively-chosen modular neck. For example, the surgeon may desire a change in at least one of the variables, e.g., leg length, offset, and/or anteversion. The present disclosure allows the surgeon to quickly and easily select a different modular neck based on an evaluation of one of the variables without requiring reevaluation of the other variables.

In one form thereof, the present invention provides a modular orthopaedic system including a stem and a plurality of modular necks. Each of the plurality of modular necks includes a stem end and a head end having a center point. The stem end of each modular neck is configured to couple to the stem and the head end of each modular neck is configured to couple to at least one head. The plurality of modular necks is configured to arrange the center points of the head ends in a grid pattern relative to the stem, wherein, with the at least one head operatively coupled to the plurality of modular necks and the plurality of modular necks operatively coupled to the stem, the plurality of modular necks is configured to arrange the at least one head in the grid pattern relative to the stem.

In another form thereof, the present invention provides a modular orthopaedic system configured for implantation with a stem, the orthopaedic system including a plurality of modular necks. Each of the plurality of modular necks is configured to couple to the stem and includes a leg length measured proximally from the stem and an offset measured medially from the stem, the leg lengths of the plurality of modular necks varying independently from the offsets of the plurality of modular necks.

In yet another form thereof, the present invention provides a modular orthopaedic system including a stem, a first modular neck, a second modular neck, and a third modular neck. The first modular neck is configured to couple to the stem, the first modular neck including a first leg length relative to the stem and a first offset relative to the stem. The second modular neck is configured to couple to the stem, the second modular neck including a second leg length relative to the stem and a second offset relative to the stem. The third modular neck is configured to couple to the stem, the third modular neck including a third leg length relative to the stem and a third offset relative to the stem. The first leg length of the first modular neck equals the second leg length of the second modular neck but differs from the third leg length of the third modular neck, and the first offset of the first modular neck equals the third offset of the third modular neck but differs from the second offset of the second modular neck.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 5B is a plan view of another subset of the system of modular necks used in the method illustrated in FIG. 2;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

The present invention generally provides modular neck components for hip implants having independent variables associated with physical characteristics of the implant, including leg length, offset, and anteversion. During surgery, the surgeon may be confronted with a need to change a preoperatively-chosen modular neck. For example, the surgeon may desire a change in at least one of the variables, e.g., leg length, offset, and/or anteversion. The present disclosure allows the surgeon to quickly and easily select a different modular neck based on an evaluation of one of the variables without requiring reevaluation of the other variables. An exemplary method of the present disclosure may include preoperative planning in which a template including a grid coordinate system is used, which advantageously provides an intuitive system for the surgeon both preoperatively and during surgery.

Figure 1:
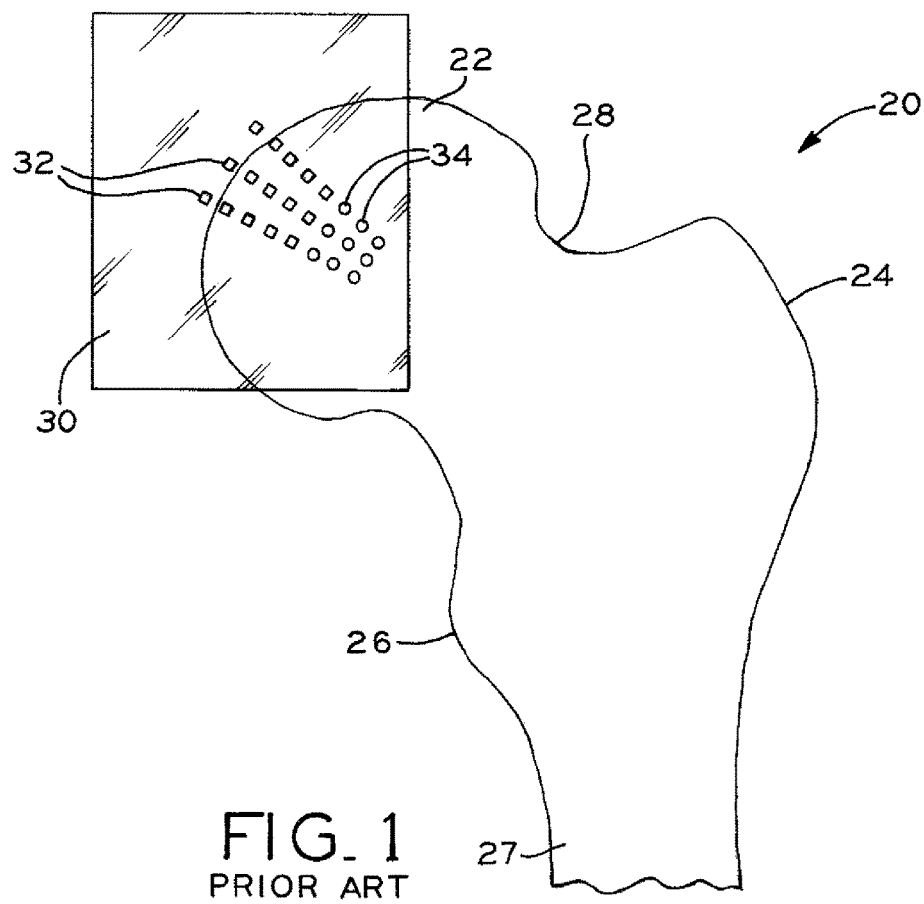
FIG. 1 is an image of a proximal femur, further showing a portion of a template of a known system overlaid on the image.
Figure 2:
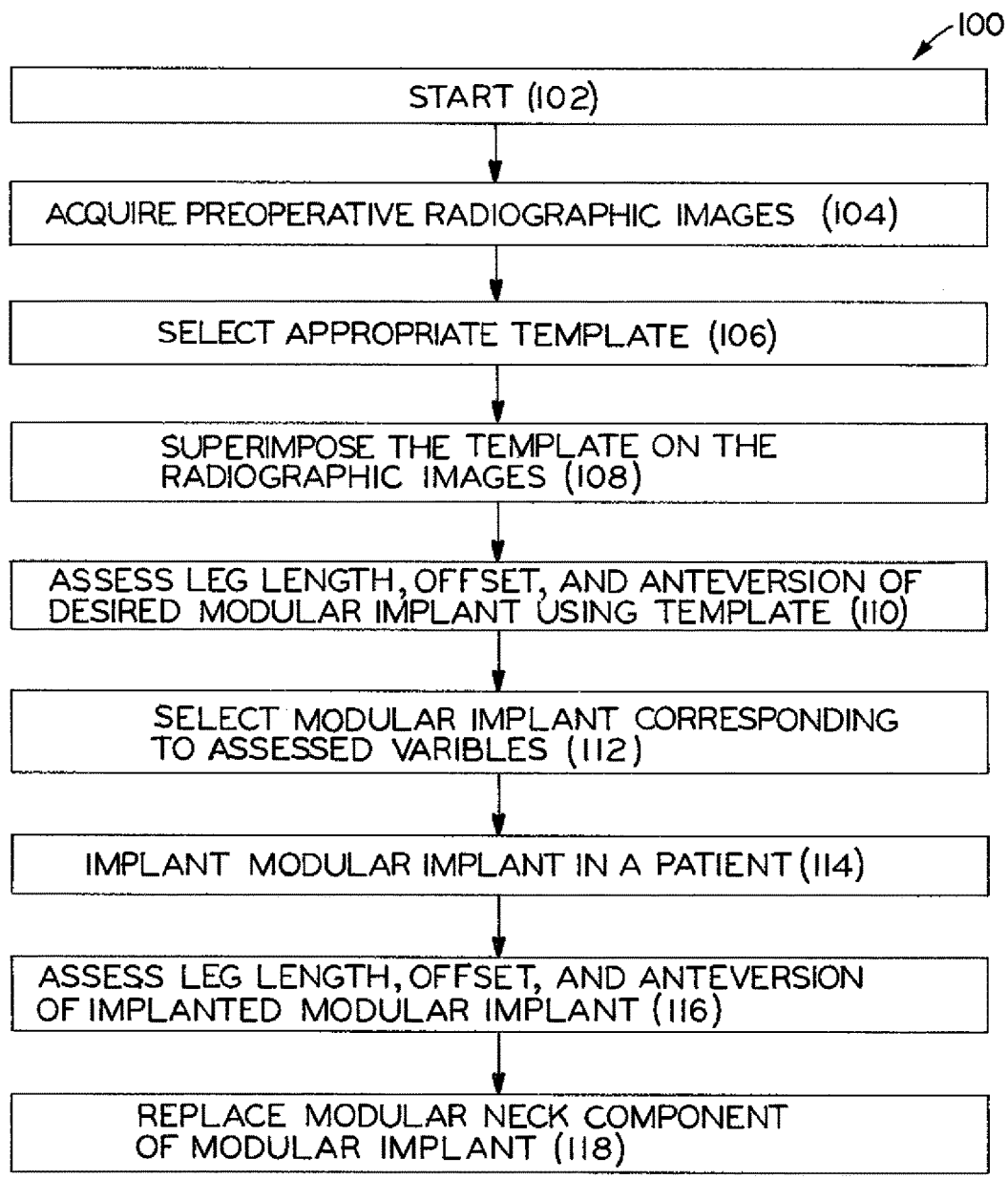
FIG. 2 is a flow chart illustrating steps of a method according to one embodiment of the present invention.

Referring to FIG. 2, a flow chart illustrating steps of method 100 is shown and includes several steps beginning with step 102. Step 102 includes preparing a patient (not shown) for the surgical procedure, e.g., collecting information and past medical history. In step 104, the surgeon or a surgeon's assistant will acquire at least one image of the appropriate portion of the hip region of the patient, e.g., at least a portion of the femur and the hip joint. The image may be a radiographic image such as an X-ray image or fluoroscopic image, for example, or, alternatively, a computed tomography (CT) image, a magnetic resonance image (MRI), or any other suitable image. Typical images for a hip replacement procedure may be taken along two different directions. For example, anterior/posterior (A/P) and lateral pelvic images may be taken of the hip joint.

Figure 3:
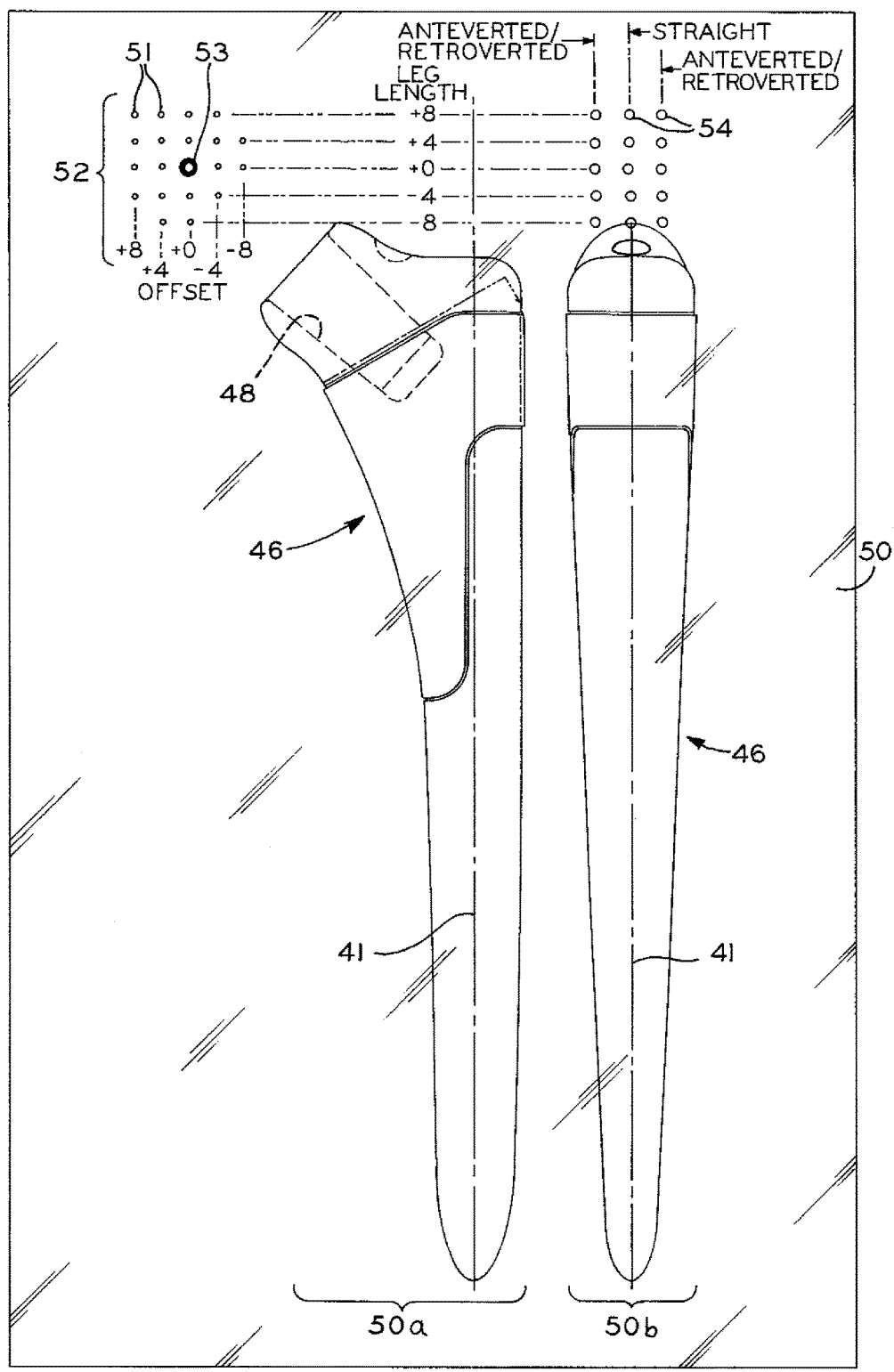
FIG. 3 is an image of a template according to one embodiment of the present invention.

Referring now to FIG. 3, a template 50 is shown which may be used in conjunction with the images to preoperatively plan a surgical procedure in order to perform the joint replacement/restoration. Template 50 may be constructed of a piece of transparent plastic or other suitable material which may be overlaid on the image of the hip portion of the patient. Template 50 may include a plurality of reference points 51 forming a grid coordinate system, for example, a Cartesian coordinate system, including a pattern of intersecting horizontal and vertical indicators or lines that provide coordinates for locating points. Reference points 51 may be formed of ink deposits on the transparent plastic, or, alternatively or in combination with the ink deposits, reference points 51 may be formed as cutouts in the transparent plastic to allow the surgeon to mark directly on the acquired image where the ideal center of rotation of the femoral head of the hip implant should be located. The grid 52 of template 50 may include leg length being measured along the "y-axis" and offset being measured along the "x-axis." Alternatively, leg length may be measured along the "x-axis" and offset may be measured along the "y-axis." Template 50 may also include graphic representations of a femoral stem component of hip implant 40 (FIG. 6), i.e., stem 46 (FIG. 6), including recess 48 shown in dashed lines in FIGS. 3 and 6. The representation of stem 46 may be formed of conventional ink on the transparent plastic. A plurality or system of templates 50 may be provided corresponding to each available size or type of femoral stem component of the hip implant system.

As shown in FIG. 3, template 50 may also include reference points 54 corresponding to the lateral pelvic view of the hip portion of the patient and which represent a third axial or cylindrical component corresponding to the anteversion component of the hip implant. Reference points 54, which are arranged in three planes, may represent an anteverted neck, a straight neck, or a retroverted neck. The planes of reference points 54 may represent the "z-axis" of grid 52 in the Cartesian coordinate system, or, alternatively, the third component may be represented in a cylindrical or polar coordinate system in which, when viewed from an end view of the proximal end of the femur, the planes in which reference points 54 are situated are arranged in a fan-shaped arrangement. More or less planes of reference points 54 may be included to accommodate a greater number of anteversion components, if needed.

In step 106, the surgeon selects the template 50 corresponding to the femoral stem component of the hip implant to be used in the surgical procedure. Template 50 may be chosen in a conventional manner such that the representation of stem 46 on template 50 substantially fills the intramedullary canal of femoral shaft 27 of the image, such that the actual femoral stem component of the hip implant will correctly fit the intramedullary canal of the actual femur.

Figure 4:
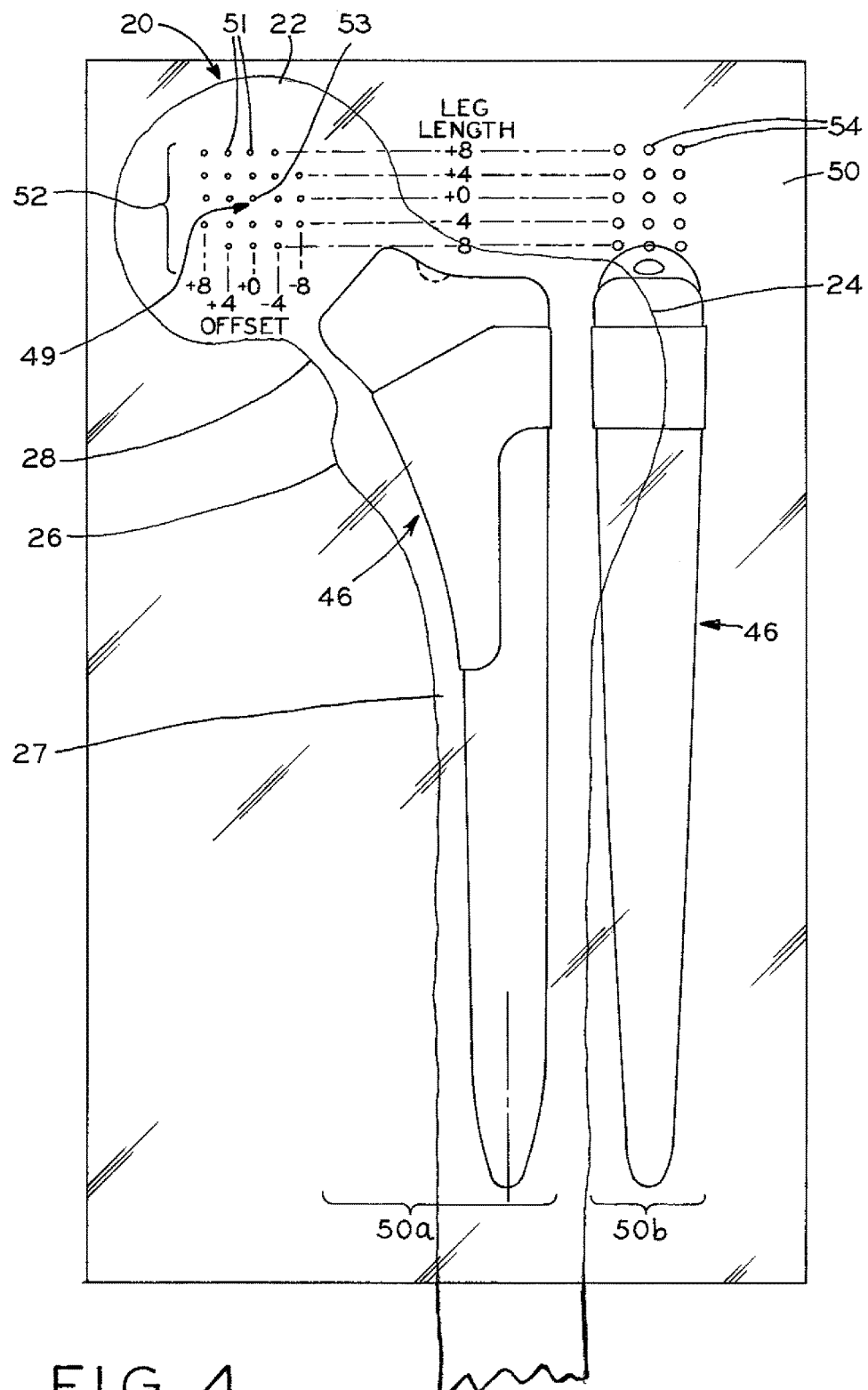
FIG. 4 is a perspective view of the template of FIG. 3 overlaid over the image of a proximal femur.

In step 108 and as shown in FIG. 4, the surgeon superimposes the correct template 50 on the acquired image. In step 110, template 50 may be used by the surgeon to determine the desired leg length and offset when using portion 50a of template 50 corresponding to the A/P pelvic view and to determine the desired anteversion and/or leg length when using portion 50b of template 50 corresponding to the lateral pelvic view. For the purposes of this document, offset is measured along a line drawn substantially perpendicular to longitudinal axis 41 of femoral stem 46. The surgeon orients the representation of stem 46 on template 50 to align with the intramedullary canal of the image of femoral shaft 27. When the surgeon is using portion 50*a* of template 50 corresponding to the A/P pelvic view, the surgeon orients origin 53 of grid 52 at the location at which the surgeon desires center 49 of head 42 of modular neck 44 (FIG. 6) to be located. This location of center 49 may not necessarily coincide with the original center of femoral head 22 prior to surgery because the condition of femoral head 22 may dictate a different center for the head of the modular implant component. For example, if the original femoral head 22 is severely deteriorated or is badly misshapen, the surgeon may desire a different center for the head of the modular implant than the current center for the original femoral head 22. Also, the surgeon may wish to correct some problem, e.g., laxity correction or bone alignment correction, which may cause the center for the head of the modular implant to be different than the center of femoral head 22. In an exemplary procedure, origin 53 coincides with center 49, as shown in FIG. 4. The surgeon then assesses or evaluates where center 49 should be located on grid 52 of template 50. This evaluation permits the surgeon to obtain the preoperatively-planned values for the offset and the leg length for the modular neck component of the hip implant.

Still referring to step 110 and FIG. 4, when the surgeon is using portion 50*b* of template 50 corresponding to the lateral pelvic view, the surgeon chooses a desired anteversion component from the planes of reference points 54. The surgeon again orients the representation of stem 46 on template 50 to align with the intramedullary canal of the image of femoral shaft 27, in the manner described above. The surgeon may use the planes of reference points 54 to determine the desired anteversion component for the modular neck of the hip implant. In an exemplary procedure, the surgeon will determine the anteversion component first, and then determine the necessary leg length and offset values for the preoperative plan of the procedure.

In step 110, the surgeon may mark directly on the image where center 49 of head 42 of modular neck 44 (FIG. 6) will be located and/or what anteversion component is necessary. In step 112, the surgeon then selects a modular neck 44 from system 60 (FIGS. 5A-5C) corresponding to the assessed variables of leg length, offset, and anteversion in the manner described below.

Figure 6:
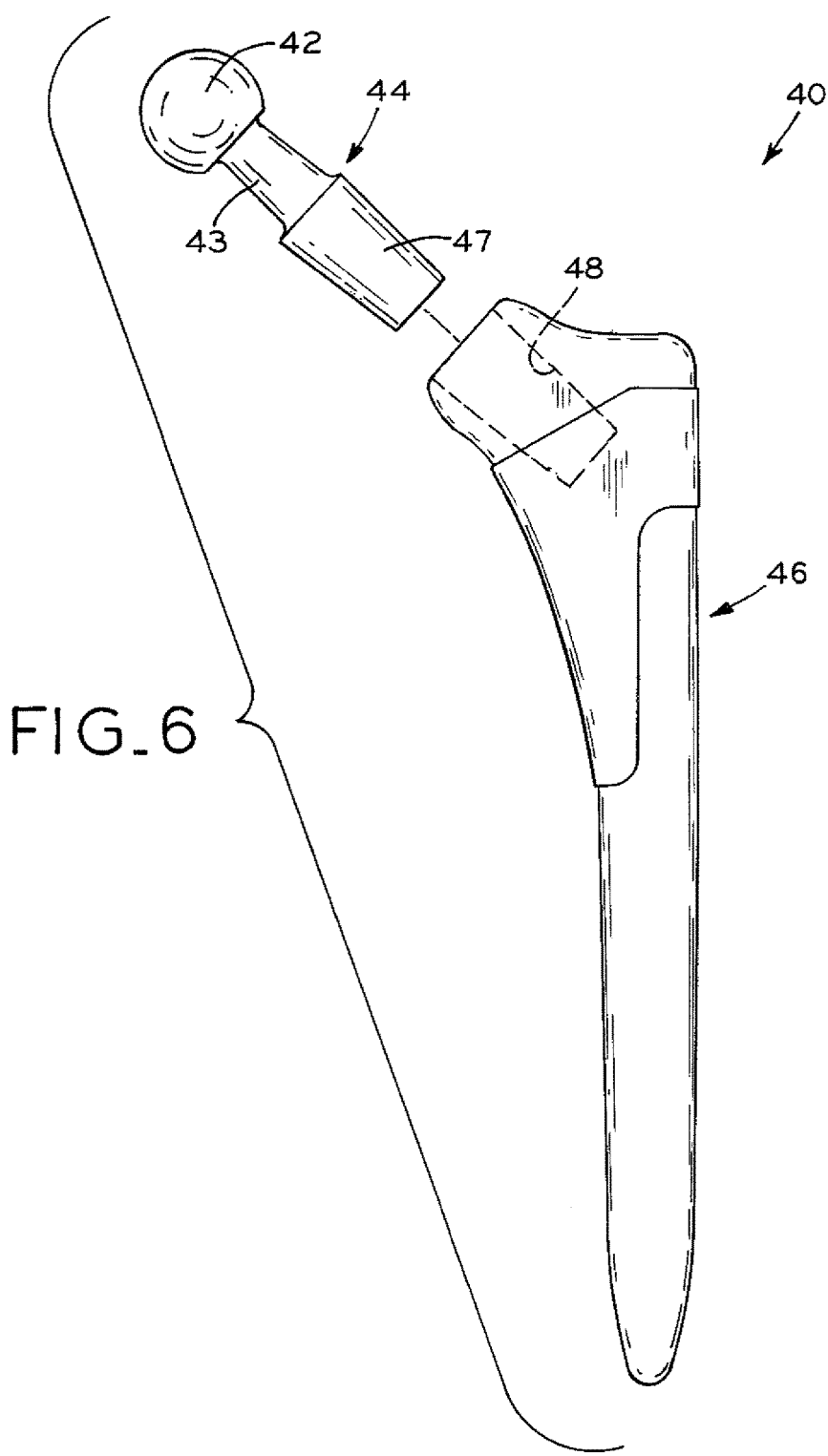
FIG. 6 is an exploded view of a modular implant.

Alternatively, template 50 may be a template on a computer screen in a computer assisted surgery (CAS) system. The surgeon may superimpose the computer generated template 50 in the CAS system on the image of the proximal femur to determine the optimal position of center 49 of head 42 of a modular neck 44 (FIG. 6). In one such embodiment, advantageously, both views, i.e., A/P and lateral, may be simultaneously viewed in the CAS system and template 50 may be superimposed thereon to allow the surgeon to simultaneously assess all three variables, i.e., anteversion, leg length, and offset.

During surgery and as shown in step 114, a preoperatively-chosen femoral stem 46 of hip implant 40 (FIG. 6) is implanted into a patient's prepared intramedullary canal by a conventional surgical technique. The surgeon may then provisionally implant the preoperatively-chosen modular neck 44 (FIG. 6) which has been chosen by the surgeon to provide the optimum result for the particular patient, in the manner described above. Modular neck 44 (FIG. 6) may include head 42, neck portion 43, and tapered portion 47 shaped to mate with recess 48 in femoral stem 46. Head 42 may be integrally formed with neck 44 or head 42 may be a modular component attached to neck portion 43 of neck 44. Advantageously, the femoral stem 46 (FIG. 6) of hip implant 40 (FIG. 6) is equipped to accept a number of different modular neck components. Thus, the leg length, anteversion, and offset of the hip implant can be changed without requiring removal of femoral stem 46.

In step 116, the surgeon may trial the provisionally implanted modular neck 44 (FIG. 6) to verify or confirm the preoperative plan and associated results. At this point, the surgeon will assess several variables, for example, leg length, offset, and anteversion, associated with the hip implant and the physical anatomy of the patient. This assessment may be completed via a conventional surgical technique, for example, moving the joint through a range of motion. The surgeon may observe that more leg length is necessary, but that the offset and anteversion are satisfactory. The present method advantageously allows the surgeon to select a new modular neck based only on the change in leg length without affecting the offset and anteversion. Similarly, the surgeon may observe that more offset is necessary, but that the leg length and anteversion are satisfactory. The present method advantageously allows the surgeon to select a new modular neck based only on the change in offset without affecting the leg length and anteversion. Because the leg length and offset changes are based on a grid coordinate system, the surgeon can easily and intuitively select a new modular neck component based on a leg length change and/or an offset change without requiring an extensive lookup table or complicated mathematical conversion calculations to ensure that no other variables are being changed undesirably.

Similarly, the surgeon may observe that a different anteversion component is necessary, but that the leg length and offset are satisfactory. The present method advantageously allows the surgeon to select a new modular neck based only on the change in anteversion without affecting the leg length and offset. Because the anteversion component is based on a grid coordinate system, similar to leg length and offset, described above, or, alternatively, on a polar coordinate system, the surgeon can easily and intuitively select a new modular neck component based on a change in anteversion without requiring an extensive lookup table or complicated mathematical conversion calculations to ensure that no other variables are being changed undesirably.

After the surgeon determines the desired change, the surgeon may employ system 60 (FIGS. 5A-5C), described below, to choose a different modular neck 44 to provide more optimum results.

Figure 5A:
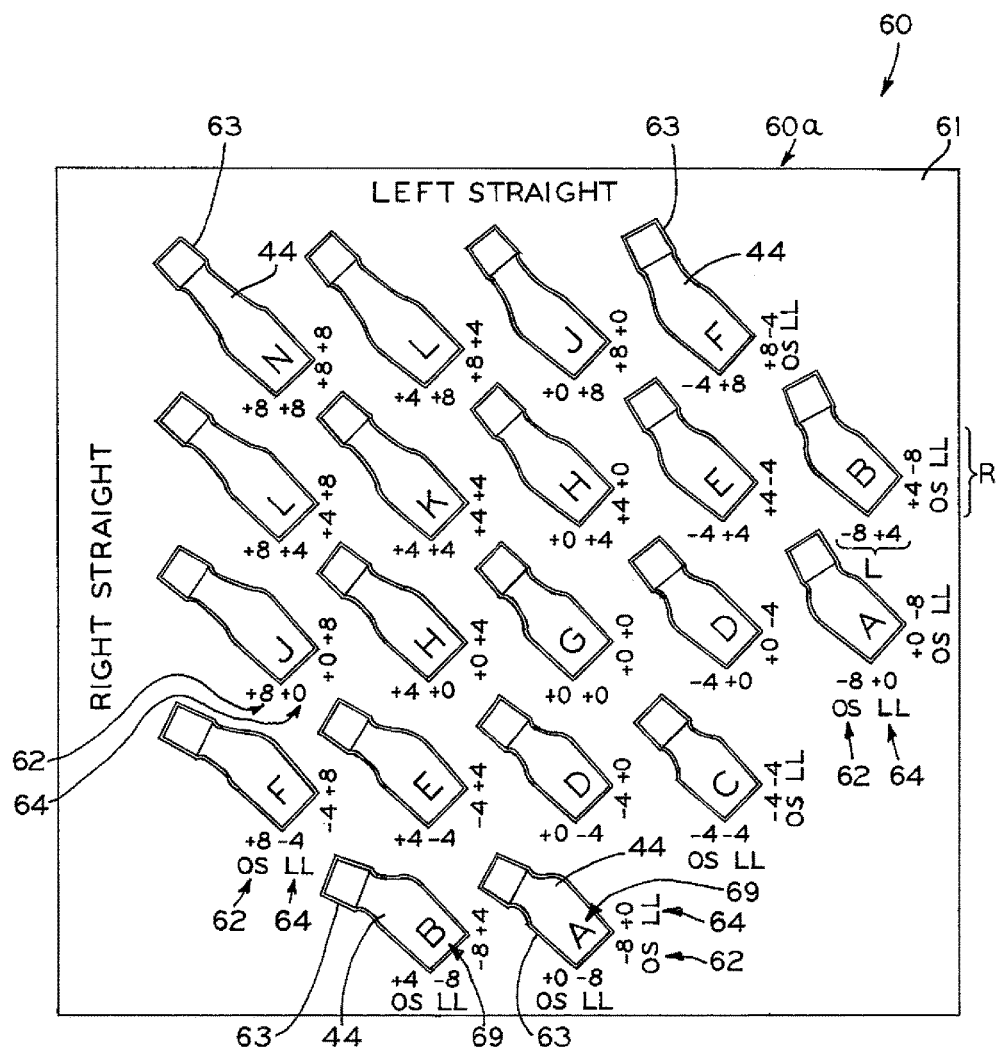
FIG. 5A is a plan view of a subset of a system of modular necks used in the method illustrated in FIG. 2.
Figure 5C:
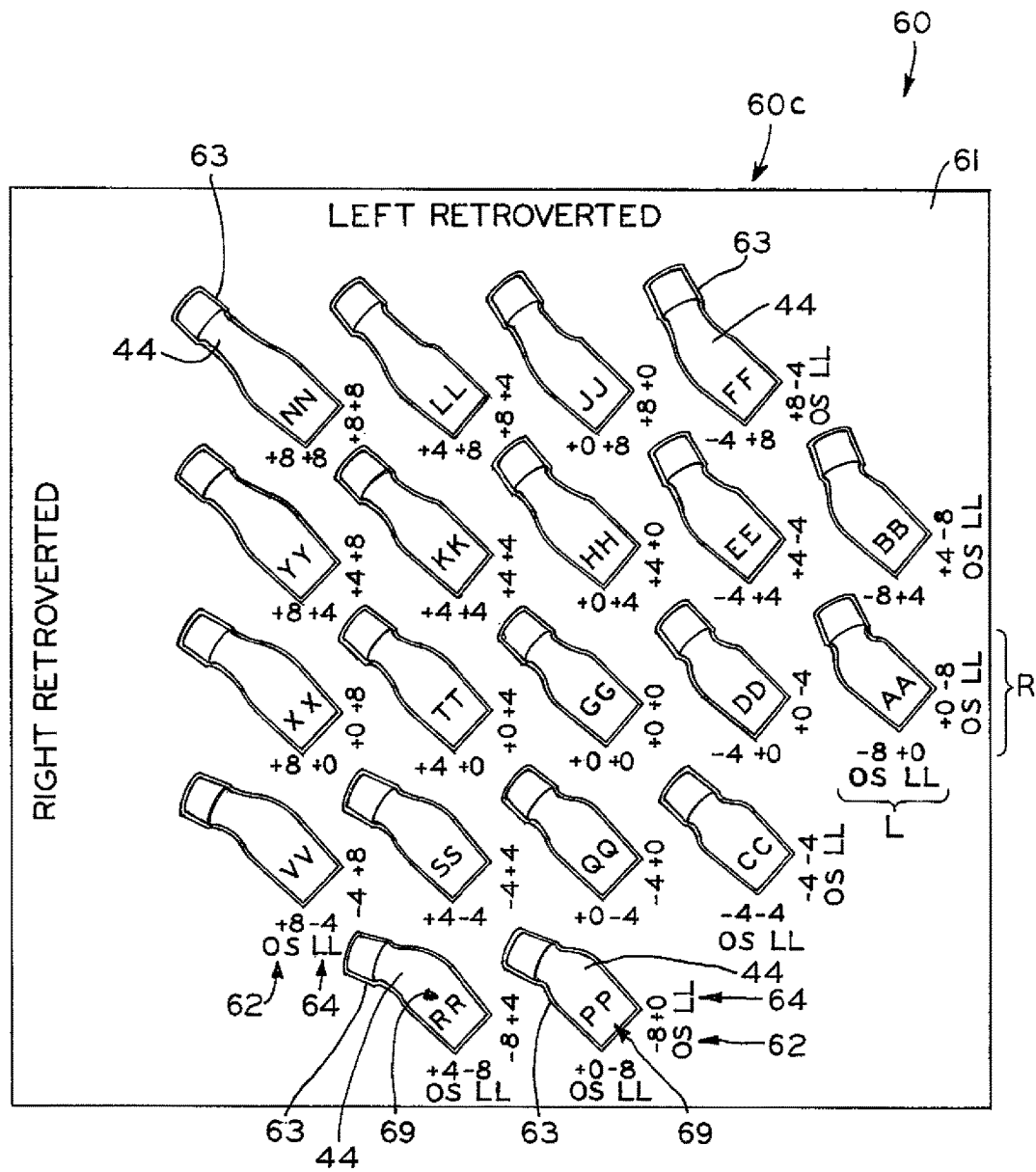
FIG. 5C is a plan view of yet another subset of the system of modular necks used in the method illustrated in FIG. 2.

Referring now to FIGS. 5A-5C, system 60 is arranged to include a plurality of modular necks 44 with varying dimensions suitable for different leg length, offset, and anteversion dimensions. In one embodiment, system 60 may include container 61 with a plurality of compartments 63 for physically housing each modular neck 44 in system 60, wherein each modular neck 44 is held in respective compartments 63 and the surgeon or an assistant selects a modular neck 44 from a compartment 63 in container 61. Each neck 44 may include reference identifier 69. In an alternative embodiment, system 60 may be a graphical representation of the plurality of modular necks 44 arranged in an organized arrangement, e.g., a Cartesian coordinate system. In this embodiment, the surgeon may select a modular neck 44 and corresponding reference identifier 69, for example, from the graphical representation, and reference identifier 69 may then be used by a surgical assistant, for example, to retrieve the desired modular neck 44 which corresponds to the surgeon's desired choice and reference identifier 69 from a central location at which the modular necks 44 are stored.

A subset of system 60 may be provided and arranged in container 61. Alternatively, a plurality of subsets of system 60 may be provided and arranged in at least one container 61. System 60 is arranged such that all necks 44 within a given subset of necks correspond to a particular anteversion component. Each subset may have a different anteversion component, thereby permitting a surgeon to independently assess the desired anteversion component and have an identical subset of necks 44 for each anteversion component. For example, the anteversion component may be, for example, anteverted, straight, or retroverted. Thus, for example, referring to FIG. 5A, subset 60a of necks 44 in system 60 may correspond to straight necks. Referring to FIG. 5B, subset 60b of necks 44 in system 60 may correspond to anteverted necks. Similarly, referring to FIG. 5C, subset 60c of necks 44 in system 60 may correspond to retroverted necks. System 60 may include as many subsets of necks 44 that correspond to the desired number of choices of the anteversion component, for example, system 60 may include additional subsets corresponding to greater extremes of anteverted and retroverted necks.

Still referring to FIGS. 5A-5C, for each neck 44 in each subset 60a, 60b, 60c of system 60, system 60 includes a pair of identifying coordinates corresponding to leg length and offset. For example, the number represented by offset component 62 corresponds to offset and the number represented by leg length component 64 corresponds to leg length. The Cartesian coordinates represented by offset component 62 and leg length component 64 may be represented by the following coordinates: (±offset, ±leg length). If origin 53 does coincide with center 49 during the preoperative planning, then the surgeon may likely choose a modular neck 44 with the following coordinates in step 112: (+0, +0). If origin 53 does not coincide with center 49 during the preoperative planning due to, for example, a defect in femoral head 22, then the surgeon may choose a modular neck with coordinates different from (+0, +0) in step 112.

Each subset 60a, 60b, 60c may include two sets of pairs of identifying coordinates corresponding to leg length and offset. Each set corresponds to either a right hip or a left hip. Advantageously, as shown in FIGS. 5A-5C, the surgeon need only rotate container 61 ninety degrees to switch between a system used for the left hip and the right hip. For example, as shown in FIG. 5A, the left hip pair of coordinates is identified by the letter L and the right hip pair of coordinates is identified by the letter R. Furthermore, as identified at the top of container 61, the anteversion component includes a designation "right" or "left" depending on which hip those necks 44 are to be used for. For example, if the surgeon needs a straight neck for a left hip, then the surgeon rotates container 61 including subset 60a until "LEFT STRAIGHT" appears at the top of container 61, as shown in FIG. 5A, at which point the offset and leg length coordinates are positioned below each respective neck 44. Alternatively, the offset and leg length coordinates may be positioned above each respective neck 44.

Intraoperatively, if the surgeon does not want any change in offset but needs a change in leg length, the surgeon will choose a new neck 44 having the following coordinates: (preoperatively-planned offset value, preoperatively-planned leg length value±change in leg length) from a particular subset according to the chosen anteversion component. Similarly, if the surgeon does not want any change in leg length but needs a change in offset, the surgeon will choose a neck 44 having the following coordinates: (preoperatively-planned offset value±change in offset, preoperatively-planned leg length value) from a particular subset according to the chosen anteversion component.

Advantageously, arranging the plurality of modular necks 44 in each subset 60a, 60b, 60c of system 60 in a Cartesian coordinate grid allows the surgeon to easily and intuitively intraoperatively choose a modular neck 44 which corresponds to an independent change in leg length, offset, or anteversion. The surgeon may use a fluoroscopic or other image-guided system (not shown) to facilitate the assessment of the change in leg length, offset, and/or anteversion, as described above, or, alternatively, the surgeon may simply manually/visually determine the desired change in leg length, offset, and/or anteversion, and subsequently choose a neck 44 from a subset of system 60 corresponding to the desired change.

In one example, if the surgeon determines in step 116 that more or less leg length is desired but that the offset and anteversion are satisfactory, the surgeon may select a different modular neck 44 from a subset of system 60 which corresponds to the desired change. For example, if the surgeon needs no change in offset and 4 millimeters (mm) more of leg length, the surgeon chooses the neck with the following coordinates from a subset of system 60 corresponding to the satisfactory anteversion component: (preoperatively-planned offset value, preoperatively-planned leg length value plus 4). Subsequently, the surgeon implants neck 44 into the femoral stem component of the hip implant. The surgeon may similarly choose a different neck 44 depending on how much change in leg length was desired.

In another example, if the surgeon determines in step 116 that less leg length and more offset are desired but the anteversion is satisfactory, the surgeon may select a different modular neck 44 from a subset of system 60 which corresponds to the desired change. For example, if the surgeon needs 4 mm more of offset and 4 mm less of leg length, the surgeon chooses the neck with the following coordinates from a subset of system 60 corresponding to the satisfactory anteversion component: (preoperatively-planned offset value plus 4, preoperatively-planned leg length value minus 4). Subsequently, the surgeon implants neck 44 into the femoral stem component of the hip implant. The surgeon may similarly choose a different neck 44 depending on how much change in leg length and/or offset was desired.

In yet another example, if the surgeon determines in step 116 that leg length and offset are satisfactory but the anteversion needs changed, the surgeon may select a different modular neck 44 from a subset of system 60 which corresponds to the desired change. For example, if the surgeon needs to change from a retroverted neck to a straight neck, the surgeon will select neck 44 from subset 60a of system 60 corresponding to a straight neck and having the desired leg length and offset.

In step 118, the different neck 44 chosen by the assessment of leg length, offset, and anteversion in step 116 is implanted into the stem component of the hip implant.

Although illustrated throughout as having intervals of 4 mm for both offset and leg length, system 60 could be arranged to have intervals of any dimension to accommodate the needs of a particular patient or the desires of a particular surgeon. For example, the interval could be 1, 2, 3, 4, or 5 mm, or any fraction thereof, for both offset and leg length.

The above-described concept has generally been described as a system having three variables, i.e., leg length, offset, and anteversion. The system has been described in which one of these three variables, i.e., the anteversion component, is constant for any given subset of implants having various offsets and leg lengths. For example, the surgeon may pre-operatively choose a desired anteversion component, which may not change intraoperatively, and then need only choose various modular necks 44 from the subset corresponding to the desired anteversion component of system 60 based only on offset and leg length. Alternatively, the system may be constructed such that leg length is the constant variable and the implants of each subset of system 60 are arranged to have identical leg lengths and varying offset and anteversion components. In another alternative embodiment, the system may be constructed such that offset is the constant variable and the implants of each subset of system 60 are arranged to have identical offsets and varying leg lengths and anteversion components.

Although described throughout with respect to a hip implant, the method could be utilized in any procedure which uses modular components, for example, but not limited to, shoulder implant procedures, knee implant procedures, etc.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A modular orthopaedic system presentable to a surgeon during an orthopaedic surgical procedure to allow the surgeon to select a modular neck from a plurality of modular necks during the orthopaedic surgical procedure, the modular orthopaedic system comprising:
   a stem; and
   a plurality of modular necks which makes up the total number of modular necks in the modular orthopaedic system for presentation to a surgeon during an orthopaedic surgical procedure, each of the plurality of modular necks comprising a stem end and a head end having a center point, the stem end of each modular neck interchangeably coupleable to the stem, said modular necks structured such that, when the plurality of modular necks are superimposed with respect to one another in a common orientation with said stem ends coupled to the stem, the center points of the head ends are arranged in a grid pattern relative to the stem, the grid pattern having a plurality of leg length axes that are equally spaced from one another and which extend proximally/distally relative to the stem and a plurality of offset axes that are equally spaced from one another and which extend medially/laterally relative to the stem, the leg length axes extending perpendicularly to the offset axes, wherein the center point of the head end of each of the plurality of modular necks comprises a leg length dimension locatable on one of the plurality of leg length axes and an offset dimension locatable on one of the plurality of offset axes.

2. The modular orthopaedic system of claim 1, wherein the plurality of modular necks are femoral necks.

3. The modular orthopaedic system of claim 1, further comprising another stem configured to couple to the plurality of modular necks, wherein the stems are provided in different sizes.

4. The modular orthopaedic system of claim 1, wherein the head end of each of the plurality of modular necks is removably coupleable to at least one modular head.

5. The modular orthopaedic system of claim 1, wherein the head end of each of the plurality of modular necks comprises an integral head.

6. The modular orthopaedic system of claim 1, wherein the grid pattern includes an anteversion axis that extends anteriorly/posteriorly relative to the stem and perpendicularly to the leg length axes and the offset axes.

7. The modular orthopaedic system of claim 1, wherein the grid pattern has a plurality of anteversion axes that are equally spaced from one another and which extend anteriorly/posteriorly relative to the stem, said anteversion axes extending perpendicularly to the leg length axes and the offset axes.

8. The modular orthopaedic system of claim 1, wherein the grid pattern in which the center points of the head ends are arranged has four or five leg length axes and an equal number of offset axes with more than one center point being positioned on each of said four or five leg length axes and on each of said offset axes, and wherein the leg length axes are equally spaced from one another a first distance of 1 millimeter to 5 millimeters, and wherein the offset axes are equally spaced from one another a second distance that equals the first distance.

9. The modular orthopaedic system of claim 1, further comprising a case including a plurality of receptacles, each of the plurality of receptacles sized to receive a corresponding one of the plurality of modular necks, and each of the plurality of receptacles including a left leg identifier that is visible when the case is in a first position and a right leg identifier that is visible when the case is rotated ninety degrees from the first position to a second position, the left leg identifier of each receptacle identifying a location of the corresponding modular neck when implanted in a patient's left leg and the right leg identifier of each receptacle identifying a location of the corresponding modular neck when implanted in a patient's right leg.

10. A modular orthopaedic system presentable to a surgeon during an orthopaedic surgical procedure to allow the surgeon to select a modular neck from a plurality of modular necks for coupling the selected modular neck to a stem during the orthopaedic surgical procedure, the modular orthopaedic system comprising:
   a plurality of modular necks which makes up the total number of modular necks in the modular orthopaedic system for presentation to a surgeon during an orthopaedic surgical procedure, each of the plurality of modular necks comprising a head end with a center point, each of the plurality of modular necks configured to interchangeably couple to the stem and when so coupled comprising a leg length dimension measured proximally from the stem to said center point and an offset dimension measured medially from the stem to said center point in a direction orthogonal to the leg length dimension, wherein, for each of the modular necks in the modular orthopaedic system, the leg length dimension and the offset dimension are together referenceable to an individual reference point on a two-dimensional Cartesian coordinate grid when the plurality of modular necks are superimposed with respect to one another in a common orientation relative to said stem, with all individual reference points on said two-dimensional Cartesian coordinate grid being equally spaced from any adjacent individual reference point on said two-dimensional Cartesian coordinate grid, wherein the plurality of modular necks includes at least two modular necks having the same leg length dimension but different offset dimensions and at least two modular necks having the same offset dimension but different leg length dimensions.

11. The modular orthopaedic system of claim 10, wherein each of the plurality of modular necks when coupled to the stem further comprises an anteversion dimension measured anteriorly from the stem to said center point, the anteversion dimensions of the plurality of modular necks varying independently from the leg length dimensions and the offset dimensions of the plurality of modular necks.

12. The modular orthopaedic system of claim 11, wherein the anteversion dimensions of the plurality of modular necks are measured orthogonally to the leg length dimensions of the plurality of modular necks and orthogonally to the offset dimensions of the plurality of modular necks.

13. The modular orthopaedic system of claim 10, further comprising a modular head configured to couple to each of the plurality of modular necks.

14. The modular orthopaedic system of claim 10, wherein all individual reference points on said two-dimensional Cartesian coordinate grid are equally spaced from any adjacent individual reference point on said two-dimensional Cartesian coordinate grid a distance of 1 millimeter to 5 millimeters.

15. The modular orthopaedic system of claim 14, wherein the plurality of modular necks making up the total number of modular necks in the modular orthopaedic system for presentation to a surgeon during an orthopaedic surgical procedure generates four or five different leg length dimensions and an equal number of different offset dimensions within the modular orthopaedic system.

16. A modular orthopaedic system presentable to a surgeon during a surgical procedure to facilitate selection of a modular neck from a plurality of modular necks, the modular orthopaedic system comprising:

a stem; and
a plurality of modular necks, each of the plurality of modular necks comprising a stem end and a head end having a center point, the stem end of each modular neck removably coupleable to the stem, each of the plurality of modular necks comprising a first dimension and a second dimension when coupled to the stem, wherein the plurality of modular necks includes at least two modular necks having the same value for the first dimension but varying values for the second dimension and at least two modular necks having the same value for the second dimension but varying values for the first dimension, wherein, for each of the plurality of modular necks, the first dimension and the second dimension are together referenceable to an individual reference point on a two-dimensional coordinate grid, and each of the individual reference points is equally spaced from any adjacent individual reference point.

17. The modular orthopaedic system of claim 16, wherein the first dimension is a leg length, measured proximally from the stem to the center point, and the second dimension is an offset dimension measured medially from the stem to the center point in a direction orthogonal to the leg length.

18. The modular implant of claim 16, wherein the plurality of modular necks comprises a first subset of necks, a second subset of necks, and a third subset of necks, the first subset configured for an anteverted orientation, the second subset configured for a straight orientation, and the third subset configured for a retroverted orientation.

19. The modular orthopaedic system of claim 16, wherein the equal spacing between adjacent individual reference points on the two-dimensional coordinate grid is a distance of 1 millimeter to 5 millimeters.

* * * * *